US009492377B2

(12) United States Patent
Mogna et al.

(10) Patent No.: US 9,492,377 B2
(45) Date of Patent: Nov. 15, 2016

(54) EFFERVESCENT COMPOSITION IN SOLID FORM FOR USE IN VAGINAL APPLICATIONS FOR THE TREATMENT OF VAGINAL INFECTIONS

(75) Inventors: Giovanni Mogna, Novara (IT); Gian Paolo Strozzi, Novara (IT); Luca Mogna, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 0 days.

(21) Appl. No.: 13/982,255

(22) PCT Filed: Jan. 24, 2012

(86) PCT No.: PCT/IB2012/000095
§ 371 (c)(1),
(2), (4) Date: Nov. 12, 2013

(87) PCT Pub. No.: WO2012/101500
PCT Pub. Date: Aug. 2, 2012

(65) Prior Publication Data
US 2014/0065115 A1 Mar. 6, 2014

(30) Foreign Application Priority Data

Jan. 28, 2011 (IT) ............... MI2011A0107
Mar. 1, 2011 (IT) ............... MI2011A0316

(51) Int. Cl.
| A01N 63/00 | (2006.01) |
| A01N 65/00 | (2009.01) |
| A61K 9/00 | (2006.01) |
| A61K 9/46 | (2006.01) |
| A61K 9/20 | (2006.01) |
| A61K 35/747 | (2015.01) |
| A61K 35/742 | (2015.01) |
| A61K 47/02 | (2006.01) |
| A61K 47/12 | (2006.01) |

(52) U.S. Cl.
CPC ........... *A61K 9/0034* (2013.01); *A61K 9/0007* (2013.01); *A61K 9/205* (2013.01); *A61K 9/2054* (2013.01); *A61K 35/742* (2013.01); *A61K 35/747* (2013.01); *A61K 47/02* (2013.01); *A61K 47/12* (2013.01)

(58) Field of Classification Search
CPC ............... A01N 63/00; A01N 65/00
See application file for complete search history.

(56) References Cited

U.S. PATENT DOCUMENTS

| 3,819,838 | A | 6/1974 | Smith et al. |
| 4,187,321 | A | 2/1980 | Mutai et al. |
| 4,332,790 | A | 6/1982 | Sozzi et al. |
| 4,670,272 | A | 6/1987 | Chen et al. |
| 4,853,211 | A | 8/1989 | Kurobe et al. |
| 2004/0185032 | A1 | 9/2004 | Burrell |
| 2005/0095232 | A1 | 5/2005 | Volkmann |
| 2006/0039973 | A1* | 2/2006 | Aldritt ........... A61K 31/715 424/466 |
| 2006/0121571 | A1 | 6/2006 | Klaenhammer et al. |
| 2006/0233774 | A1 | 10/2006 | Lim et al. |
| 2007/0207132 | A1 | 9/2007 | Speelmans et al. |
| 2007/0269515 | A1* | 11/2007 | Henriksen et al. ........... 424/480 |
| 2008/0175899 | A1 | 7/2008 | Ross et al. |
| 2008/0187628 | A1 | 8/2008 | Champion et al. |
| 2010/0092440 | A1* | 4/2010 | Strozzi et al. ............ 424/93.44 |
| 2011/0178488 | A1 | 7/2011 | Balazs |

FOREIGN PATENT DOCUMENTS

| CA | 2221426 | 5/1998 |
| CA | 2739345 | 4/2010 |
| CN | 1345589 A | 4/2002 |
| EA | 011952 | 9/2004 |
| EA | 010981 | 2/2007 |
| EP | 0002692 | 7/1979 |
| EP | 0845350 | 6/1998 |
| EP | 0956858 | 11/1999 |
| EP | 1600060 | 11/2005 |
| EP | 1600061 | 11/2005 |
| EP | 2000530 | 12/2008 |
| EP | 2269465 | 1/2011 |
| EP | 2338976 | 6/2011 |
| EP | 2626076 | 8/2013 |
| JP | A-2010-511033 | 4/2010 |
| KZ | 11784 | 8/2002 |
| KZ | 17967 | 6/2011 |
| RU | 02150268 | 6/2000 |
| RU | 2338511 C2 | 11/2008 |
| WO | 94/12142 | 6/1994 |
| WO | 99/49877 | 10/1999 |
| WO | 00/72855 | 12/2000 |
| WO | 2004/089278 | 10/2004 |
| WO | 2004/101770 | 11/2004 |
| WO | 2006/013588 | 2/2006 |
| WO | 2007/100765 | 9/2007 |
| WO | 2007/125558 | 11/2007 |

(Continued)

OTHER PUBLICATIONS

Ronnqvist et al. (*Lactobacillus fermentum* Ess-1 with unique growth inhibition of vulvo-vaginal candidiasis pathogens. Journal of Medical Microbiology (2007), 56, 1500-1504).*
PCT International Search Report mailed on Dec. 17, 2012 for PCT/IB2012/001745 filed on Sep. 10, 2012 in the name of Probiotical S.p.A.
Written Opinion mailed on Dec. 17, 2012 for PCT/IB2012/001745 filed on Sep. 10, 2012 in the name of Probiotical S.p.A.
International Search Report mailed on Dec. 3, 2012 for PCT/IB2012/001741 filed on Sep. 10, 2012 in the name of Giovanni Mogna.

(Continued)

*Primary Examiner* — Karen Cochrane Carlson
*Assistant Examiner* — Natalie Moss
(74) *Attorney, Agent, or Firm* — Steinfl & Bruno LLP

(57) ABSTRACT

The present invention relates to an effervescent composition in solid form for use in vaginal applications for the treatment of vaginal infections.

16 Claims, No Drawings

(56) References Cited

FOREIGN PATENT DOCUMENTS

| WO | 2008/038075 | | 4/2008 | | |
|----|----|----|----|----|----|
| WO | 2008/065492 | | 6/2008 | | |
| WO | WO 2008/065492 | A2 * | 6/2008 | ............... | A61K 9/14 |
| WO | 2008/153377 | | 12/2008 | | |
| WO | 2009/138218 | | 11/2009 | | |
| WO | 2010/023248 | | 3/2010 | | |
| WO | 2010/099824 | | 9/2010 | | |
| WO | 2010/103374 | | 9/2010 | | |
| WO | 2010/133761 | | 11/2010 | | |
| WO | 2011/012932 | | 2/2011 | | |
| WO | 2011/017040 | | 2/2011 | | |
| WO | 2012/001440 | | 1/2012 | | |
| WO | 2012/101500 | | 8/2012 | | |
| WO | 2010/136891 | | 3/2013 | | |
| WO | 2013/034974 | | 3/2013 | | |
| WO | 2013/034975 | | 3/2013 | | |
| WO | 2013/050831 | | 4/2013 | | |

OTHER PUBLICATIONS

Written Opinion mailed on Dec. 3, 2012 for PCT/IB2012/001741 filed on Sep. 10, 2012 in the name of Giovanni Mogna.

PCT International Preliminary Report on Patentability issued on Jul. 30, 2013 for PCT/IB2012/000095 filed on Jan. 24, 2012 in the name of Probiotical S.p.A.

International Search Report mailed on Dec. 3, 2012 for International patent application PCT/IB2012/001848 filed on Sep. 21, 2012 in the name of Probiotical S.p.A.

International Written Opinion mailed on Dec. 3, 2012 for International patent application PCT/IB2012/001848 filed on Sep. 21, 2012 in the name of Probiotical S.p.A.

PCT International Search Report mailed on Sep. 21, 2012 for PCT/IB2012/000895 filed on May 9, 2012 in the name of Probiotical S.p.A.

PCT Written Opinion mailed on Sep. 21, 2012 for PCT/IB2012/000895 filed on May 9, 2012 in the name of Probiotical S.p.A.

PCT International Preliminary Report on Patentability issued on Nov. 12, 2012 for PCT/IB2012/000895 filed on May 9, 2012 in the name of Probiotical S.p.A.

PCT International Search Report mailed on Aug. 24, 2012 for PCT/IB2012/000897 filed on May 9, 2012 in the name of Probiotical S.p.A.

PCT Written Opinion mailed on Aug. 24, 2012 for PCT/IB2012/000897 filed on May 9, 2012 in the name of Probiotical S.p.A.

PCT International Preliminary Report on Patentability issued on Nov. 12, 2013 for PCT/IB2012/000897 filed on May 9, 2012 in the name of Probiotical S.p.A.

PCT International Search Report mailed on Sep. 27, 2012 for PCT/IB2012/000907 filed on May 9, 2012 in the name of Probiotical S.p.A.

PCT Written Opinion mailed on Sep. 27, 2012 for PCT/IB2012/000907 filed on May 9, 2012 in the name of Probiotical S.p.A.

PCT International Preliminary Report on Patentability issued on Nov. 12, 2013 for PCT/IB2012/000907 filed on May 9, 2012 in the name of Probiotical S.p.A.

PCT International Search Report mailed on Dec. 16, 2011for PCT/IB2011/000561 filed on Mar. 17, 2011 in the name of Probiotical S.p.A.

PCT Written Opinion mailed on Dec. 16, 2011for PCT/IB2011/000561 filed on Mar. 17, 2011 in the name of Probiotical S.p.A.

PCT International Preliminary Report on Patentability mailed on Sep. 17, 2013 for PCT/IB2011/000561 filed on Mar. 17, 2011 in the name of Probiotical S.p.A.

Search Report mailed on Nov. 11, 2011 for IT MI20110792 filed on May 9, 2011 in the name of Probiotical S.p.A.

Written Opinion mailed on Nov. 11, 2011 for IT MI20110792 filed on May 9, 2011 in the name of Probiotical S.p.A.

First Examination Report issued Apr. 28, 2014 for NZ IP No. 614002 filed on Aug. 6, 2013 in the name of Probiotical S.p.A.

Restriction Requirement mailed on Jan. 7, 2014 for U.S. Appl. No. 14/005,821, filed Nov. 6, 2013.

Non-Final Office Action mailed on Jun. 5, 2014 for U.S. Appl. No. 14/005,821, filed Nov. 6, 2013.

A. Amaretti, et al. "Antioxidant properties of potentially probiotic bacteria: in vitro and in vivo activities", Applied Microbiology and Biotechnology. vol. 97 (2), 2013, pp. 809-817.

M. Candela, et al. "Interaction of probiotic *Lactobacillus* and *Bifidobacterium* strains with human intestinal epithelial cells: Adhesion properties, competition against enteropathogens and modulation of IL-8 production", International Journal of Food Microbiology, vol. 125 (3), pp. 286-292, Jul. 2008.

C P Champagne, et al: "The determination of viable counts in probiotic cultures microencapsulated by spray-coating", Food Microbiology, Academic Press Ltd, London, GB, vol. 27, No. 8, Dec. 1, 2010, pp. 1104-1111. Abstract Only.

A. Cheikhyoussef, et al. "Antimicrobial activity and partial characterization of bacteriocin-like inhibitory substances (BLIS) produced by *Bifidobacterium infantis* BCRC 14602", Food Control, Butterworth, London, GB, vol. 20 (6), pp. 553-559, Jun. 2009.

M.C. Collado, et al: "Probiotic Strains and Their Combination Inhibit in Vitro Adhesion of Pathogens to Pig Intestinal Mucosa", Current Microbiology, Springer-Verlag, NE, vol. 55, No. 3, Jul. 25, 2007, pp. 260-265. Abstract Only.

M. Del Piano, et al. "Evaluation of the intestinal colonization by microencapsulated probiotic bacteria in comparison with the same uncoated strains", Journal of Clinical Gastroenterology, vol. 44, pp. S42-S46, Sep. 2010.

Mario Del Piano, et al: "Is microencapsulation the future of probiotic preparations? The increased efficacy of gastro-protected probiotics", Gut Microbes Mar.-Apr. 2011 LNKDPUBMED:21637030, vol. 2, No. 2, Mar. 2011, pp. 120-123.

K.A. Eaton, et al: "Probiotic *Lactobacillus reuteri* Ameliorates Disease Due to Enterohemorrhagic *Escherichia coli* in Germfree Mice", Infection and Immunity, vol. 79, No. 1, Oct. 25, 2010, pp. 185-191.

M.F. Fernandez, et al: "Probiotic properties of human lactobacilli strains to be used in the gastrointestinal tract", Journal of Applied Microbiology, Oxford, GB, vol. 94, No. 3, Online Feb. 12, 2003, pp. 449-455.

FAO/WHO. *Guidelines for the Evaluation of Probiotics in Food.* Apr. 30/May 1, 2002, 11 pgs.

M. Gotteland, et al, "Systematic review: are probiotics useful in controlling gastric colonization by *Helicobacter pylori*? "Alimentary Pharmacology & Therapeutics, vol. 23, pp. 1077-1086, Apr. 15, 2006.

M Gueimonde, et al: "Adhesion and competitive inhibition and displacement of human enteropathogens by selected lactobacilli", Food Research International, Elsevier Applied Science, Barking, GB, vol. 39, No. 4, May 1, 2006, pp. 467-471. Summary Citation.

H.Q. Huynh, et al: "N-Acetylcysteine, a Novel Treatment for *Helicobacter pylori* Infection", Digestive Disease and Sciences, Kluwer Academic Publishers-Plenum Publishers, NE, vol. 49, No. 11-12, Nov. 1, 2004, pp. 1853-1861.

P Hütt, et al: "Antagonistic activity of probioitic lactobacilli and bifidobacteria aganst entero- and uropathogens", Journal of Applied Microbiology, vol. 100, No. 6, Jun. 2006, pp. 1324-1332.

K.C. Johnson-Henry, et al: "*Lactobacillus rhamnosus* Strain GG Prevents Enterohemorrhagic *Escherichia coli* O157:H7-Induced Changes in Epithelial Barrier Function", Infection and Immunity, vol. 76, No. 4, Apr. 1, 2008, pp. 1340-1348.

J. Kim, et al. "Antimicrobial effect of *Bifidobacterium breve* and *Bifidobacterium infantis* against *Salmonella* Typhimurium KCTC 1925 and *E.coli* O157:H7 ATCC 43895", Food Science and Biotechnology, Korean Society of Food Science and Technology, vol. 11 (1), pp. 89-92, Jan. 2002.

Likotrafiti, et al. "Molecular Identification and Anti-pathogenic Activities of Putative Probiotic Bacteria Isolated from Faeces of Healthy Elderly Individuals", Microbial Ecology in Health and Disease, 16, pp. 105-112 (2004).

(56) References Cited

OTHER PUBLICATIONS

Meei-Yn Lin, et al., "Axtioxidative effect of intestinal bacteria *Bifidobacterium longum* ATCC 15708 and *Lactobacillus acidophilus* ATCC 4356", Digestive Diseases & Sciences 2000, 45: 1617-1622.

Meei-Yn. Lin, et al., "Inhibition of lipid peroxidation by *Lactobacillus acidophilus* and *Bifidobacterium longum*", J. Agricultural & Food Chemistry 1999, 47: 3661-3664.

M.A. Losada, et al. "Towards a healthier diet for the colon: the influence of fructooligosaccharides and lactobacilli on intestinal health", Nutrition Research, vol. 22, Jan. 2002, pp. 71-84.

Hong Lu, et al: "New development in the mechanistic understanding of peptic ulcer diseases", Drug Discovery Today: Disease Mechanisms, Elsevier, vol. 3, No. 4, 2006, pp. 431-437.

F. Lutgendorff, et al., "Probiotics enhance pancreatic glutathione biosynthesis and reduce oxidative stress in experimental acute pancreatitis", Am. J. Physiol. Gastrointest. Liver Physiol., 2008, vol. 295; G1111-G1121.

M. Malecka, "Antioxidant properties of the unsaponifiable matter isolated from tomato seeds, oat grains and wheat germ oil" Food Chemistry, 2002, vol. 79, pp. 327-330.

A Marchese, et al.: "Effect of fosfomycin alone and in combination with N-acetylcysteine on *E. coli* biofilms", International Journal of Antimicrobial Agents, vol. 22, Oct. 1, 2003, Suppl. 2, (Oct. 1, 2003), pp. 95-100.

L.V. McFarland: "Meta-analysis of probiotics for the prevention of antibiotic associated diarrhea and the treatment of *Clostridium difficile* disease", The American Journal of Gastroenterology Apr. 2006 LNKD-PUBMED:16635227, vol. 101, No. 4, Apr. 2006, pp. 812-822.

M. Modesto, et al. "Resistance to freezing and freeze-drying storage processes of potential probiotic bifidobacteria", Annals of Microbiology, 54 (1), pp. 43-48 (2004).

L. Peran, et al., A comparative study of the preventative effects exerted by three probiotics, *Bifidobacterium lactis*, *Lactobacillus casei* and *Lactobacillus acidophilus*, in the TNBS model of rat colitis, J. Applied Microbiology 2007, 103: 836-844.

V. Rada, et al: "Susceptibility of bifidobacteria to lysozyme as a possible selection criterion for probiotic bifidobacterial strains", Biotechnology Letters, Springer Netherlands, Dordrecht, vol. 32, No. 3, Nov. 27, 2009, pp. 451-455. Abstract Only.

V. Rada, et al. "Susceptibility of bifidobacteria to nisin", Letters in Applied Microbiology, vol. 26, 1998, pp. 123-125.

C. Santini et al., "Characterization of probiotic strains: an application as feed additives in poultry against *Campylobacter jejuni*", Int J Food Microbiol., 2010, 141 Suppl 1:S98-108. Epub Apr. 8, 2010 Abstract Only.

S. Torrian I, et al. "Differentiation of *Lactobacillus plantarum*, *L. pentosus*, and *L. paraplantarum* by recA Gene Sequence Analysis and Multiplex PCR Assay with recA Gene-Derived Primers", Appl. Environ. Microbiol. 2001. vol. 67 (8), pp. 3450-3454.

J. Walter, et al. "Detection and Identification of Gastrointestinal *Lactobacillus* Species by Using Denaturing Gradient Gel Electrophoresis and Species-Specific PCR Primers", Appl. Environ. Microbiol. 2000. vol. 66 (1), pp. 297-303.

Dan Yang Ying, et al: "Microencapsulated Lactobacillus rhamnosus GG Powders: Relationship of Powder Physical Properties to Probiotic Survival during Storage", Journal of Food Science, vol. 75, No. 9, Nov. 1, 2010, pp. E588-E595. Abstract Only.

S. Zanoni, et al., Growth kinetics on oligo- and polysaccharides and promising features of three antioxidative potential probiotic strains, J. Applied Microbiology 2008, 105: 1266-1276.

L. Zhang, et al., "Evaluation of Lactobacillus rhamnosus GG using an *Escherichia coli* K88 model of piglet diarrhoea: Effects on diarrhoea incidence, faecal microflora and immune responses", Veterinary Microbiology, Elsevier BV. NL, vol. 141, No. 1-2, Feb. 24, 2010, pp. 142-148. Epub Sep. 11, 2009. Abstract Only.

Office Action issued Jul. 15, 2014 for KZ Application No. 2013/1615.1 filed on Jan. 24, 2012 by Tagbergenova Alma Taishevna et al.

The EFSA Journal, "Opinion of the Scientific Panel on Additives and Products or Substances used in Animal Feed on the updating of the criteria used in the assessment of bacteria for resistance to antibiotics of human and veterinary importance", 2005, 223, pp. 1-12.

European Commission—Health & Consumer Protection Directorate-General, "Opinion of the Scientific Committee on Animal Nutrition on the Criteria for Assessing the Safety of Micro-Organisms Resistant to Antibiotics of Human Clinical and Veterinary Importance", 2002, pp. 1-20.

Labia Irene Ivette Ouoba, et al., "Resistance of potential probiotic lactic acid bacteria and bifidobacteria of African and European origin to antimicrobials: Determination and transferability of the resistance genes to other bacteria", International Journal of Food Microbiology, 2008, 121, 217-224.

D. Infante Pina, et al., "Prevalence and dietetic management of mild gastrointestinal disorders in milk-fed infants", World Journal of Gastroenterology, 2008, vol. 14, No. 2: 248-254.

PCT International Search Report mailed on Mar. 29, 2012 for PCT/IB2012/000095 filed on Jan. 24, 2012 in the name of Probiotical S.p.A.

PCT Written Opinion mailed on Mar. 29, 2012 for PCT/IB2012/000095 filed on Jan. 24, 2012 in the name of Probiotical S.p.A.

Grimoud, J. et al., "In vitro screening of probiotic lactic acid bacteria and prebiotic glucooligosaccharides to select effective synbiotics", Anaerobe, 16 (2010) 493-500.

MacFarlane, S. et al., "Review article: prebiotics in the gastrointestinal tract", Alimentary Pharmacology & Therapeutics, 2006, 24, 701-714.

Milani, C. et al., "Comparative Genomics of *Bifidobacterium animalis* subsp. *lactis* Reveals a Strict Monophyletic Bifidobacterial Taxon", Applied and Environmental Microbiology, 79(14), 2013, 4304-4315.

Okombo, J. et al., "Probiotic-induced reduction of gastrointestinal oxalate absorption in healthy subjects", Urol Res (2010), 38: 169-178.

"Sachet" Webpage from merriam-webster.com, Oct. 7, 2011, accessed via WayBackMachine.com. 1 page.

First Office Action issued on Nov. 4, 2014 for Chinese Patent Application No. 201280022854.9 filed on May 9, 2012 in the name of Probiotical S.p.A. (English + Chinese). 15 pages.

Final Office Action mailed on Dec. 30, 2014 for U.S. Appl. No. 14/005,821, filed Nov. 6, 2013 in the name of Giovanni Mogna. 30 pages.

Restriction Requirement mailed on Feb. 4, 2015 for U.S. Appl. No. 14/116,996, filed Dec. 18, 2013 in the name of Giovanni Mogna. 11 pages.

Non-Final Office Action mailed on May 21, 2015 for U.S. Appl. No. 14/116,996, filed Dec. 18, 2013 in the name of Giovanni Mogna. 11 pages.

Restriction Requirement mailed on Mar. 11, 2015 for U.S. Appl. No. 14/116,999, filed Dec. 20, 2013 in the name of Giovanni Mogna. 12 pages.

Non-Final Office Action mailed on Jun. 16, 2015 for U.S. Appl. No. 14/116,999, filed Dec. 20, 2013 in the name of Giovanni Mogna. 29 pages.

Restriction Requirement mailed on Feb. 20, 2015 for U.S. Appl. No. 14/117,003, filed Dec. 27, 2013 in the name of Giovanni Mogna. 9 pages.

"7th Probiotics & Prebiotics—new food", Universita Urbaniana, Rome. Poster 66: "Effectiveness of the Two Microorganisms L. Fermentum LF15 and L. Plantarum LP01, Formulated in Slow Release Vaginal Tablets, in Women Affected by Bacterial Vaginosis (BV): A Pilot Study", pp. Cover-50, Jul. 2013.

Al-Wahsh, I. et al. "Acute probiotic ingestion reduces gastrointestinal oxalate absorption in healthy subjects." Urological Research: A Journal of Clinical and Laboratory Investigation in Urolithiasis and Related Areas, vol. 40(3), pp. 191-196. Aug. 2011.

Castro-Leyva, V. et al. "Preserved Ex Vivo Inflammatory Status in Decidual Cells from Women with Preterm Labor and Subclinical Intrauterine Infection." PLOS ONE, vol. 7 (8), e43605, pp. 1-6. Aug. 2012.

(56) References Cited

OTHER PUBLICATIONS

Grill et al. Canadian Journal of Microbiology. Oct. 2000, 46, pp. 878-884.
Hoesl, C. E. et al. "The Probiotic Approach: An Alternative Treatment Option in Urology" European Urology, vol. 47, No. 3, pp. 288-296. Mar. 2005.
Klaver et al. "The Assumed assimilation of cholesterol by lactobacilli and Bifidobacterium bifidum is due to their bile salt-deconjugating activity" Appl Environ Microbiology, 1993, vol. 59, No. 4, pp. 1120-1124.
Mogna, L. et al. "Assessment of the in vitro inhibitory activity of specific probiotic bacteria against different *Escherichia coli* strains." Journal of Clinical Gastroenterology, vol. 46, Supp. 1, pp. S29-S32. Oct. 2012.
Pascual, L. et al. "Vaginal Colonization and Activity of the Probiotic Bacterium *Lactobacillus fermentum* L23 in a Murine Model of Vaginal Tract Infection", Journal of Medical Microbiology, vol. 59, No. 3, pp. 360-364, Nov. 2009.
S. Keersmaecker et al. "Strong antimicrobial activity of Lactobacillus rhamnosus GG against *Salmonella typhimurium* is due to accumulation of lactic acid" Federation of European Microbiological Societies Microbiology Letters 259. (2006) 89-96.
Saggioro, A. "Probiotics in the Treatment of Irritable Bowel Syndrome." Journal of Clinical Gastroenterology, vol. 38(6), pp. S104-106. Jul. 2004.
Strus, M. et al. "Studies on the Effects of Pro Biotic *Lactobacillus* Mixture Given Orally on Vaginal and Rectal Colonization and on Parameters of Vaginal Health in Women with Intermediate Vaginal Flora" Eurpoean Journal of Obstetrics Gynecology and Reproductive Biology, vol. 163, No. 2 pp. 210-215. Aug. 2012.
Vicariotto, F. et al: "65: Effectiveness Of An Association Of A Cranberry Dried Extract, D-Mannose And The Three Microorganisms L. Plantarum Lp01, L. Paracasei, Lpc09 And S. Thermophilus St10 in Women Affected by Cystitis: A Pilot Study", 7th Probiotics & Prebiotics New Foods, pp. 1-52, Jul. 2013.
Wikipedia, "Strain (biology)" https://en.wikipedia.org/wiki/Strain (biology) Retrieved on Nov. 3, 2015. 2 pgs.
International Preliminary Report on Patentability for PCT/IB2012/001745 filed on Sep. 10, 2012 in the name of Probiotical North America Inc. mail date: Mar. 12, 2014 8 pages.
International Search Report issued for PCT/IB2014/000731 filed on May 14, 2014 in the name of Probiotical S.P.A. Mail date: Jul. 25, 2014 7 pages.
International Search Report issued for PCT/IB2014/000739 filed on May 14, 2014 in the name of Probiotical S.P.A. Mail date: Jul. 31, 2014 8 pages.
Written Opinion issued for PCT/IB2014/000731 filed on May 14, 2014 in the name of Probiotical S.P.A. Mail date: Jul. 25, 2014 10 pages.
Written Opinion issued for PCT/IB2014/000739 filed on May 14, 2014 in the name of Probiotical S.P.A. Mail date: Jul. 31, 2014 11 pages.
European Patent Office Communication pursuant to Article 94(3) EPC in relation to Application No. 12 780 278.3-1401. Mailed Jun. 6, 2015 4 pages.
Restriction Requirement issued for U.S. Appl. No. 14/344,021, filed May 9, 2014 in the name of Giovanni Mogna. mail date: Aug. 14, 2015. 7 pages.
Wikipedia "Pharmaceutical Drug" Updated Apr. 15, 2016. Downloaded from the internet Apr. 21, 2016. 11 pages.
Office Action for Russian Patent Application No. 2013137656/15(056766) filed Jan. 24, 2012 on behalf of Probiotical S.P.A. Mail Date: Mar. 18, 2016. 10 pages. (Russian original + English translation).
Opposition to Ecuadorian Patent Application SP-2013-13082 on behalf of Alafar. 14 pages. (Spanish original + English translation).
Japanese Patent Office Official Action for Japanese Patent Application No. 2013-550962. Mail Date: Dec. 1, 2015. 10 pages. (Japanese original + English translation).
Alam, M. et al. "Development and Evaluation of Acid-buffering Bioadhesive Vaginal Tablet for Mixed Vaginal Infections" AAPS PharmSciTech 2007; vol. 8; No. 4; Article 109, pp. E1-E8.
First Office Action for Chinese Patent Application No. 201280015994.3 Issue Date: Mar. 25, 2016. 23 pages. (Chinese original + English translation).
Mei, X. et al. "Manual of New Drug and Special Drug" Technology Press, $2^{nd}$ Version, Jan. 2001. 2 pages (Chinese Original. English Translation in NPL Reference No. 42.).
Guo, X. "Basics and Application of Probiotics" Science and Technology Press, $1^{st}$ Version, Oct. 2002, 2 pages (Chinese Original. English Translation in NPL Reference No. 42).
English translations of Non-Patent Literature References 40 and 1: Mei, X. "Manual of New Drug and Special Drug" Technology Press, $2^{nd}$ Version, Jan. 2001. And Guo, X. "Basics and Application of Probiotics" Oct. 2002, 2 pages.
Chilean First Examination report mailed of Feb. 12, 2016 for Chilean application No. 2013-002148 filed on Jul. 26, 2013 in the name of Probiotical S.P.A., 21 pgs. Spanish with English translation.
http://www.ub.es/legmh/capitols/sunyenegre.pdf Dr. Jose Ma Sune Negre, New Galenic Formulations to Forms of Administration (Nuevas Aportaciones Galenicas a las Formas de Administracion. En: Curos de formacion continuada para farmaceuticos de hospital. Fundacion Promocion Medica. Barcelona, 2002, 3, pp. 27-65), 3.2. 27 pgs. Spanish with English Abstract.
http://intranet.comunidadandina.org/Documentos/Gacetas/Gace722.PDF Breach Action Filed by the General Secretary of the Andean Community Against the Republic of Peru, Process 89-AI-2000 (Gaceta Oficial, del Acuerdo de Cartagena, Sumario, Tribunal de Justicia de la Comunidad Andina), Ano XVIII, Numero 722, Lima, Oct. 12, 2001, 44 pgs. Spanish with English Abstract.

\* cited by examiner

EFFERVESCENT COMPOSITION IN SOLID FORM FOR USE IN VAGINAL APPLICATIONS FOR THE TREATMENT OF VAGINAL INFECTIONS

CROSS REFERENCE TO RELATED APPLICATIONS

The present application is the US national stage of International Application PCT/IB2012/000095 filed on Jan. 24, 2012 which, in turn, claims priority to Italian Application MI2011A000107 filed on Jan. 28, 2011 and Italian Application MI2011A000316 filed on Mar. 1, 2011.

The present invention relates to an effervescent composition in solid form for use in vaginal applications for the treatment of vaginal infections.

It is well known that the composition of intestinal and urogenital microflora represents a critical point for an individual's health and wellbeing. The vaginal ecosystem consists of epithelial cells that line the vagina and uterus, glandular cells that secrete into the lumen of the organ and complex bacterial flora represented by different species of microorganisms.

These microorganisms have the ability to ferment glycogen originating from the decomposition of parabasal cells of the eutrophic vaginal mucosa, with a consequent production of lactic acid, whose final effect is the establishment and maintenance of an acidic vaginal environment (with pH values of 4-4.5 under physiological conditions).

The H+ deriving from lactic acid contribute to the formation of hydrogen peroxide. This molecule is toxic for a large number of bacterial species which lack the enzyme catalase. At the level of vaginal secretions, concentrations of 0.75-5 µg/ml are easily reached and are abundantly sufficient in order for the toxic effect to be expressed.

The combined action of hydrogen peroxide, uterine peroxidase (produced by the cervix and endometrium) and $Cl^-$ and $I^-$ ions also limits bacterial growth by directly activating polymorphonucleates, which exert a bactericidal action in epithelial intercellular spaces. In women, due to a variety of exogenous and endogenous factors, such as the intake of antibiotics, states of stress, hormonal modulations associated with pregnancy and the menstrual cycle or the intake of high concentrations of estrogen, an imbalance frequently occurs in the vaginal ecosystem. The alteration in the balance of the vaginal ecosystem leads to a prevalence of so-called "opportunistic" microorganisms (e.g. *Candida albicans* and *glabrata*) and/or pathogenic microorganisms (e.g. *Neisseria gonorrheae* and *Trichomonas vaginalis*) which can lead to candidiasis, vaginitis or forms of vaginosis.

Epidemiological data show that vaginal infections today affect over a billion women worldwide every year, with serious repercussions from a socioeconomic standpoint.

The therapy generally adopted is an antibiotic and/or fungicidal one, which usually gives good results in the short term, but shows to be incapable of preventing recurrent infections due to the ever increasing resistance of pathogens. Moreover, not all subjects who need to be treated are able to undertake and tolerate an antibiotic or fungicidal therapy.

The use of microorganisms capable of restoring the correct composition of vaginal microflora is known.

However, the mode of delivery of the microorganisms into the vaginal environment represents a very critical factor. It is known, for example, that soft gelatin capsules, usually known as soft gels, entail suspending the probiotic component in an oily matrix which, after the product's application, tends to constitute a physical barrier capable of slowing down or almost totally inhibiting the capacity of said probiotic component to colonize the vaginal mucosa. Furthermore, the oily matrix could exert a toxic effect on the microorganisms, to such a degree as to considerably reduce the number and viability thereof.

For example, the capsules may take a relatively long time to dissolve and in any case they do not assure an adequate dispersion of the active ingredient throughout the vaginal environment.

For example, hydrophilic suspensions, or hydrogels, entail a mode of application that is neither easy nor very comfortable. In fact, the subjects must remain lying down for at least 20-30 minutes after applying them so as to prevent the product from leaking out.

Finally, traditional vaginal tablets pose a problem of high mortality of the microorganisms during their manufacture and moreover they are not able to ensure an adequate distribution of microorganisms in the vaginal environment.

Thus, there remains a need to have a composition capable of delivering probiotic bacteria into the vaginal environment and ensuring a complete dispersion/distribution thereof.

Moreover, there remains a need to have a pharmaceutical form that can be easily administered and is practical to use.

In particular, there remains a need to have a composition which represents a valid alternative to antibiotic and/or fungicidal therapy and at the same represents an improvement over the known forms of administration.

The Applicant has surprisingly found that a probiotic formulation in the form of a suitably prepared solid composition is capable of solving the problems persisting in the prior art.

The subject matter of the present invention is an effervescent composition in solid form, as set forth in the appended independent claim.

Other preferred embodiments of the present invention are set forth in the appended dependent claims.

Table 1 shows the bacterial strains tested by the Applicant and which form the subject matter of the present invention.

Table 2 shows an example of a composition according to the invention.

Table 3 shows the mortality data for the probiotic bacteria according to the different pressures exerted and stability of the tablets (expressed as the half-life of the bacterial load) after 2 years of storage thereof at 25° C.

Table 4 shows a composition that is not in accordance with the present invention.

Table 5 shows a composition in tablet form that is not in accordance with the present invention.

The Applicant conducted lengthy, intense experimental research activity with the aim of identifying the optimal qualitative and quantitative composition for preparing the composition of the present invention, as well as the operating conditions for the preparation thereof.

The composition of the present invention is an effervescent composition. The effervescence is due to the formation of carbon dioxide which occurs when an acid-base system comprising an organic acid and a salt of the carbonate and/or bicarbonate anion comes into contact with the water/moisture present in the vaginal cavity. The acid-base system is capable of maintaining the intravaginal pH stable within an interval comprised from 3 to 5.5, preferably from 4 to 5. Advantageously, the intravaginal pH is comprised from 4.2 to 4.5.

The composition of the present invention is an effervescent composition in solid form. In a preferred embodiment, the organic acid is in solid form, preferably a powder or granules, and the salt of the carbonate and/or bicarbonate anion is in solid form, preferably a powder or granules.

In a preferred embodiment, the effervescent composition in solid form is in the form of a tablet, ovule, lozenge or granules.

The organic acid is selected from the group consisting of, or alternatively comprising, citric acid, malic acid, tartaric acid, fumaric acid, lactic acid and mixtures thereof. In a preferred embodiment, the organic acid is citric acid.

The Applicant has found that the use of adipic and/or ascorbic acid as the organic acid present in the aforesaid acid-base system provokes a toxic effect on the microorganisms, resulting in the mortality thereof already at the time of preparation of the composition in solid form, for example as a powder or granules. In the case of the preparation of a tablet, said mortality occurs after the components are mixed to give a composition in solid form, for example as a powder or granules, but prior to compression. Therefore, the composition of the present invention does not contain adipic acid and/or ascorbic acid.

The salt of the carbonate and/or bicarbonate anion is selected from the group consisting of or, alternatively, comprising: sodium carbonate, potassium carbonate, calcium carbonate, magnesium carbonate, sodium glycine carbonate, sodium bicarbonate, potassium bicarbonate, calcium bicarbonate, magnesium bicarbonate, sodium lactate, potassium lactate, carbonate lactate and mixtures thereof. Preferably, said salt is selected from the group consisting of or, alternatively, comprising a salt of the bicarbonate anion. In a preferred embodiment, the salt is sodium bicarbonate.

In a preferred embodiment, the amount of the salt of the carbonate or bicarbonate anion is comprised from 1 to 15% by weight, relative to the total weight of the composition. Preferably, it is comprised from 3 to 13% by weight, relative to the total weight of the composition; even more preferably, it is comprised from 4 to 12% by weight, relative to the total weight of the composition. Advantageously, it is comprised from 5 to 10% by weight, relative to the total weight of the composition.

In a preferred embodiment, the amount of sodium bicarbonate is comprised from 1 to 15% by weight, relative to the total weight of the composition. Preferably, it is comprised from 3 to 13% by weight, relative to the total weight of the composition; even more preferably it is comprised from 5 to 10% by weight, relative to the total weight of the composition. Advantageously, it is comprised from 5 to 10% by weight, relative to the total weight of the composition.

In a preferred embodiment, the acid-base system consists of citric acid and sodium bicarbonate in an amount by weight as described above.

The Applicant has found that when the salt of the carbonate or bicarbonate anion, e.g. sodium bicarbonate, is more than 15% by weight, relative to the total weight of the composition, a toxic effect is manifested against the microorganisms due to an osmotic effect.

The amount of organic acid to be used in the acid-base system is calculated once the amount of the salt of the carbonate or bicarbonate anion used in accordance with the above-described concentrations has been determined. The amount of organic acid used is stoichiometric and is a function of the salt used and solely serves the purpose of forming carbon dioxide. In the presence of said salt, the organic acid is capable of developing effervescence, due to the formation of carbon dioxide, after hydration inside the vaginal cavity.

The effervescent tablet, suitably formulated, is capable of delivering a large population of lactic bacteria for rapid colonization of the entire epithelium and vaginal mucosa. Thanks to the pH-controlled and stabilized effervescent system, the lactic bacteria are delivered into the vaginal cavity in a good physiological condition which enables them to grow and multiply.

Advantageously, the composition of the present invention, in the form of an effervescent tablet, is capable of ensuring an optimal distribution of the bacteria over the vaginal mucosa. Moreover, said composition is capable of ensuring and maintaining an anaerobic or microaerophilic environment inside the vaginal cavity thanks to the formation of carbon dioxide.

The Applicant has found that a mixture comprising or, alternatively, consisting of [microcrystalline cellulose:arabinogalactan], preferably in a ratio by weight of 1:1 to 3:1, is capable of preserving the number and viability of the cells of the microorganisms when it is desired to obtain a tablet from the composition in powder form.

In a preferred embodiment, the composition of the present invention comprises a mixture containing [microcrystalline cellulose:arabinogalactan] in a ratio by weight of 1:1 to 3:1.

Preferably, arabinogalactan derived from plants is used. Advantageously, arabinogalactan derived from larch (e.g. FiberAid®, from the Larex® range of products distributed by Lonza Inc. USA) is used.

The Applicant has likewise found that using corn starch as the aggregating substance in the composition of the present invention provides unsatisfactory results when the composition in powder form is used to prepare tablets, since the tablets obtained following compression of the powder are capped.

A mixture comprising or, alternatively, consisting of [microcrystalline cellulose:arabinogalactan] in a ratio by weight of 1:1 to 1:3, on the contrary, allows tablets to be obtained with no occurrence of capping.

Therefore, the tablets obtained from the composition of the present invention do not contain corn starch. In place of corn starch, a mixture containing [microcrystalline cellulose:arabinogalactan] is used in a ratio by weight preferably comprised from 1:1 to 3:1. The microcrystalline cellulose can be either partly or completely replaced by cellulose in powder form. Both microcrystalline cellulose and cellulose in powder form are present in the list of food additives as E460.

Arabinogalactan is a biopolymer consisting of arabinose and galactose monomers. There are two classes of arabinogalactans: those derived from plants and those of microbial origin.

The microcrystalline cellulose (or cellulose in powder form) is present in amount comprised from 2 to 45% by weight, relative to the total weight of the composition, preferably from 5 to 25%.

The arabinogalactan is present in amount comprised from 5 to 30% by weight, relative to the total weight of the composition, preferably from 10 to 20%.

Preferably, the composition of the present invention can further comprise at least one additional component selected from the group comprising: sodium carboxymethyl cellulose, anhydrous calcium hydrogen phosphate and hydroxypropyl methylcellulose.

Said at least one additional component is present in the composition of the present invention in a total amount that ranges from 3 to 70% w/w, more preferably from 6 to 40% w/w, and even more preferably from 10 to 25% w/w, relative to the total weight of the composition.

According to a preferred embodiment of the invention, the composition of the present invention further comprises magnesium stearate in an amount of 0.5% to 7% w/w, preferably 1% to 3.5% w/w, relative to the total weight of the composition.

According to a preferred embodiment of the invention, the composition of the present invention can further comprise silicon dioxide in an amount of 0.5% to 4% w/w, preferably 1% to 2% w/w, relative to the total weight of the composition.

According to a preferred embodiment of the invention, the composition of the present invention can further comprise sucrose palmitate in an amount of 0.5% to 7% w/w, preferably 1% to 3.5% w/w, relative to the total weight of the composition.

According to a preferred embodiment of the invention, the composition of the present invention can further comprise a mixture of glycerides (saponifiable fats) in an amount of 0.5% to 10% w/w, preferably 2% to 7% w/w, relative to the total weight of the composition.

According to a preferred embodiment of the invention, the composition can further comprise from 0.5% to 10% w/w, preferably from 1% to 5% w/w, of sucrose ester, the percentages being expressed relative to the total weight of the composition.

The composition of the invention is for vaginal applications for the treatment of vaginal infections such as vaginitis, vaginosis, candidiasis, gonorrhoea, herpes and venereal ulcer.

In a preferred embodiment, the composition is in the form of a tablet. Alternatively, the tablet can be coated with one or more polymer materials known in the art.

With regard to the microbial population of the formulations according to the present invention, it is advantageous to use probiotic microorganisms, used individually or in a mixture, even one consisting of different genera or species.

Probiotic microorganisms are by definition microorganisms, prevalently bacteria of human origin, which are capable of inducing beneficial effects if taken regularly in a sufficient quantity and for an adequate amount of time.

The composition of the present invention comprises at least one probiotic bacterial strain having the ability to reduce and/or eliminate the presence of pathogenic agents selected from the group comprising: *Candida albicans, Candida glabrata, Candida parapsilosis, Candida krusei, Candida tropicalis, Gardnerella vaginalis, Trichomonas vaginalis, Neisseria gonorrhoeae, Escherichia coli, Herpex simplex* and *Haemophilus ducreyi*.

Preferably, said bacterial strain belongs to at least one species selected from the group consisting of: *Lactobacillus plantarum, Lactobacillus pentosus, Lactobacillus casei, Lactobacillus casei* ssp. *paracasei, Lactobacillus rhamnosus, Lactobacillus acidophilus, Lactobacillus delbrueckii, Lactobacillus delbrueckii* ssp. *bulgaricus, Lactobacillus delbrueckii* ssp. *delbrueckii, Lactobacillus fermentum, Lactobacillus gasseri, Lactobacillus reuteri, Bifidobacterium longum, Bifidobacterium bifidum, Bifidobacterium breve, Bifidobacterium animalis* ssp. *lactis, Bifidobacterium adolescentis, Bifidobacterium pseudocatenulatum, Bifidobacterium catenulatum* or *Bifidobacterium infantis*.

Among the above-mentioned bacterial species, the bacterial strains listed in Table 1 have demonstrated to be particularly preferred.

In a preferred embodiment, the bacterial strains are selected from among: *Lactobacillus salivarius* CRL 1328, *Lactobacillus paracasei* CRL 1289, *Lactobacillus gasseri* CRL 1259, *Lactobacillus crispatus* CRL 1251, *Lactobacillus crispatus* CRL 1266, *Lactobacillus acidphilus* CRL 1294, *Lactobacillus paracasei* LPC 00, *Lactobacillus plantarum* LP 02 and *Lactobacillus fermentum* LF 10.

In a preferred embodiment, the composition of the present invention, preferably in the form of a tablet, comprises at least two strains selected from the above-mentioned group.

In a preferred embodiment, the composition of the present invention, preferably in the form of a tablet, comprises at least three strains selected from the above-mentioned group.

In a preferred embodiment, the composition of the present invention, preferably in the form of a tablet, comprises at least four strains selected from the above-mentioned group.

The strains selected from among: *Lactobacillus salivarius* CRL 1328, *Lactobacillus paracasei* CRL 1289, *Lactobacillus gasseri* CRL 1259, *Lactobacillus crispatus* CRL 1266 and *Lactobacillus fermentum* LF 10 have demonstrated to be advantageous.

In the tablets according to the invention, the microorganisms, preferably used in the form of a lyophilized culture having a viable count generally comprised from 10 to 200 billion colony forming units (CFU)/gram, are preferably present in an amount of 0.5 to 20% w/w, preferably 1 to 15% w/w, even more preferably 3 to 10% w/w, relative to the total weight of the tablet.

In one of the preferred embodiments, in order to enhance the probiotic effectiveness of the formulations according to the present invention, specific prebiotic components are introduced into the powder mixture, so that a symbiotic composition is obtained. The prebiotic component is generally a non-digestible mixture of a saccharidic nature, at least partially soluble in water or in an aqueous solution, which stimulates the growth and/or activity of one or more probiotic bacterial strains as described above. Among these prebiotic agents, dietary fibres are preferred.

Preferably, said prebiotic fibre is selected from the group comprising: fructo-oligosaccharides (FOS), galacto-oligosaccharides (GOS), trans-galactooligosaccharides (TOS), xylo-oligosaccharides (XOS), chitosan oligosaccharides (COS), α-galactosides (such as raffinose and stachyose), pectins, gums, partially hydrolyzed gums, inulin, psyllium, acacia, carob, oat or bamboo fibre, citrus fibres and, in general, fibres containing a soluble and an insoluble portion, in a variable ratio to each other.

Advantageously, said prebiotic fibre is selected from among fructo-oligosaccharides (FOS), galacto-oligosaccharides (GOS) and xylo-oligosaccharides (XOS). These fibres are not used by yeasts of the *Candida* genera, which thus lends a competitive advantage to the bacterial strains present in the composition of the present invention.

Preferably, the prebiotic component is present in the composition in an amount of up to 70% w/w, preferably comprised from 5 to 50% w/w, even more preferably from to 30% w/w, relative to the total weight of the composition.

In a preferred embodiment, the composition according to the invention can contain additional active components, e.g. vitamins, minerals, vegetable extracts or other compounds with an effect that is synergistic with or complementary to that of the population of microorganisms present in the formulations according to the invention.

Preferably, said additional active components are present in the composition in an amount of up to 70% w/w, preferably comprised from 0.5 to 40% w/w, even more preferably from 1 to 20% w/w, relative to the total weight of the composition.

The combination of technological excipients of compression and effervescence according to the present invention assures an adequate cohesiveness of the powders of the tablet and brings about the desired kinetics of release of the active ingredients after the intake thereof.

The mixing of the various components, generally in powder form, can be done by adding the components in any order whatsoever, taking care to add the culture of microorganisms, preferably in the form of a lyophilizate, as the last ingredient, to prevent the possibility that an excessive mixing time may induce a mechanical shock in the wall of the bacterial cells, with consequent suffering and reduced stability of the final product.

Formulations produced in accordance with the method of the present invention are characterized by excellent flowability, a parameter that favours uniform loading of the dies (i.e. the space dedicated to accommodating the specific amount of powder to be compressed) in the compression machines. Said compression machines typically comprise a device for loading the dies (generally represented by a hopper for delivering the powder mixture) and a metal disk of suitable radius, in whose thickness the dies themselves are obtained; these are present in variable number depending on the machine, and the step of compressing the powder takes place therein, thanks to the simultaneous, synergistic movement of two moving parts of the machine, defined as punches.

During the compression step, the lower punch defines, with its position, the volume of the die (and thus the amount of powder loaded each time), whereas the upper punch, positioned outside the die the during loading thereof with the powder mixture, is able to be lowered during the compression step and enter into contact with the powder present in the die, thus imposing, thanks to the force exerted, a more or less marked mechanical deformation on the particles making up the powder. At the end of the compression step, the upper punch rises, thus moving away from the die, and subsequently the lower punch also rises, expelling the newly formed tablet from the die.

Said compression machines further comprise a number of devices for controlling the main operating parameters (position of the lower punch at the start of the compression cycle, lowest position reached by the upper punch during the compression cycle, rotation speed of the disk in which the dies are present and so forth).

There exist alternative and rotary compression machines, according to the machine's overall operating modes and, consequently, the number of tablets it is able to produce in a given unit of time. Tablets can thus be produced using compression machines known in the art and using punches of varying shape, preferably double-radius round convex and oval punches.

The compression force applied during manufacture is evaluated by quantifying, with a hardness tester, the force required to break a tablet. Said force is measured in Kp (Kiloponds) (1 Kp=9.807 Newtons (N)). The negative effect of compression on the population of microorganisms is manifested both when the applied forces are high, for example in tablets with a hardness of 10-12 Kp, and when they are low, such as, for example, in tablets with a hardness of 5-6 Kp. The disadvantage of using high forces is a larger reduction in the number of microorganisms, whereas with low forces a reduced cohesion of the tablet is generally obtained. Advantageously, the tablets of the present invention show a compression force comprised from 5 to 12 Kp, depending on the type of tablet it is desired to obtain.

In manufacturing tests on tablets containing *L. paracasei* LPC 00, *L. acidphilus* LA 02 and *L. salivarius* CRL 1328 (table 2), the Applicant obtained very positive results both in terms of survival and in terms of subsequent stability.

In particular, a mortality ranging from 4 to 15% was observed when the compression force applied was such as to obtain tablets with a hardness comprised from 5 to 6 Kp and a mortality ranging from 10 to 25% when the compression force applied was such as to obtain tablets with a hardness comprised from 10 to 12 Kp. Another advantage of the method according to the invention is that this enables the production of sufficiently cohesive tablets even at low compression forces, for example tablets with a hardness of 5-6 Kp.

The tablets prepared in accordance with the present invention were tested in order to evaluate the disintegration time according to the European Pharmacopoeia, Ed. X, ref. 2.9.1. The friability of uncoated tablets was tested in accordance with ref. 2.9.7 and the resistance to crushing according to ref. 2.9.8.

Table 2 shows an example of a composition in accordance with the invention.

Table 3 shows the mortality data for the probiotic bacteria (composition shown in table 2) according to the different pressures exerted and the stability of the tablets (expressed as the half-life of the bacterial load) after 2 years of storage thereof at 25° C. The tablets obtained with the formulations according to the invention had a thickness of about 7.7 mm in the case of tablets with a high degree of hardness and about 8.4 mm in the case of tablets with a low degree of hardness.

In table 3, stability is expressed as the half-life of the probiotic component of the formulation, i.e. the time that elapses before the initial viable cell count is halved.

The following were also measured:
(1) Number of viable cells $1\times10^9$ CFU/g of powder expected at time zero
(2) Number of viable cells $1\times10^9$ CFU/g of powder found at time zero
(3) % mortality due to compression
(4) Number of viable cells $1\times10^9$ CFU/tablet after 2 years at 25° C.
(5) half-life in days The above data were obtained by evaluating the number of probiotic bacteria present in the powder composition and in the composition after compression using the viable plate count method, in accordance with methods known to persons skilled in the art.

In the case of the powder composition, an amount comprised from 1 to 4 grams of sample was resuspended in a suitable volume of a sterile liquid medium, generally a 0.85% sodium chloride saline solution, to which bacteriological peptone is added in a proportion of 1 g/liter.

After dissolution of the powder and subsequent homogenization with a suitable piston-driven instrument, the number of cells/ml is reduced by means of subsequent base 10 serial dilutions.

In practice, 1 ml of the most concentrated dilution is transferred each time, using a sterile pipette, into 9 ml of diluent; this operation is carried out a number of times that is sufficient to bring the quantity of microorganisms present per ml of diluent to a number comprised from 10 to 300, so that following their transfer into a Petri dish and the addition of a suitable agarized culture medium they form separate, and thus countable, colonies.

In the case of the tablets, a protocol was observed which provides for prior crushing of three to five tablets and continuance of the analysis as described above for the powder composition.

The experimental data demonstrate a low mortality both in tablets with a high degree of hardness (approximately 16.4% of the initial population) and in those with a lower degree of hardness (approximately 8.2% of the initial population). A further advantageous aspect of the composition of the present invention is improved stability, over time, of the probiotic microorganisms (probiotic component) present therein compared to the typical stability of a prior art formulation. This advantage is due to the use of a mixture containing [microcrystalline cellulose:arabinogalactan] in a ratio by weight preferably comprised from 1:1 to 3:1. This mixture is capable of greatly limiting the mechanical damage caused to the probiotic bacterial cells by the compression step and allows tablets to be obtained with no occurrence of capping.

The Applicant has found that the half-lives of the probiotic component in the powder composition and in the tablets of varying hardness manufactured with a formulation according to the invention are very similar, demonstrating the fact that the technological components used are able to minimize the mechanical damage caused by the compression step.

Advantageously, the tablets according to the invention display a high rate of survival of the probiotic microorganisms even following the compression step.

A further advantageous aspect is the ability to release carbon dioxide as the tablet disintegrates, resulting in the creation of an anaerobic or microaerophilic environment particularly favourable to vaginal colonization by the probiotics used.

The effervescence is further capable of assuring an adequate and homogeneous distribution of the probiotic active ingredient in the vaginal environment by increasing the effectiveness of colonization.

The compositions of the present invention make it possible to obtain tablets containing probiotic microorganisms which are effective and stable over time, even at non-refrigerated temperatures, because the components forming the composition have been chosen and selected with the aim of reducing mortality due to mixing and mortality due to compression without impairing the cohesion of the powder. For this reason, the composition of the present invention, preferably in the form of a tablet, contains neither adipic acid nor ascorbic acid, the amount of the salt of the carbonate or bicarbonate anion present is lower than 15% by weight, relative to the total weight of the composition, and a mixture of microcrystalline cellulose and arabinogalactan is used instead of corn starch.

The Applicant arrived at these results starting off from a composition that demonstrated to be inadequate (table 4).

The composition of table 4 shows: 80.8% mortality due to mixing, 40.5% mortality due to compression and an overall mortality (mixing+compression) of 88.6%.

The composition of table 4 shows marked mortality already at the powder level, prior to compression. The pH of dissolution (in saline in a 1:10 ratio) is not a problem, as it is equal to 5.22 for the first formulation and 5.53 for the second one.

Adipic acid was found to be toxic. But this toxicity accounts for only a certain portion of the mortality observed (about 60% of the total mortality). Ascorbic acid was found to be toxic. But this toxicity accounts for a further portion of mortality. Removing ascorbic acid from the composition of table 4 reduces mortality from 73.8 to 26.7%. Adipic acid on its own is in any case toxic (45.8% at pH 4.24); its toxicity seems to increase in the presence of ascorbic acid. Ascorbic acid thus seems to show a toxicity synergistic with that of adipic acid.

However, it is important to note that the sum of the toxicity due to adipic acid and ascorbic acid does not account for the overall mortality observed.

For this reason, the Applicant investigated the presence of other components capable of having a toxic effect with the aim of justifying the total toxicity observed in the composition of table 4.

Therefore, some other component (apart from pH, which was already considered) must justify the remaining toxicity in the same manner as adipic and ascorbic acid.

A degree of mortality was ascertained to be due to osmotic pressure, given by the bicarbonate present in an excessive amount. This mortality revealed to be equal to about 20%. Adipic acid, ascorbic acid and the osmotic effects mediated by bicarbonate are responsible for the toxicity observed. Bicarbonate in itself is not toxic: it becomes so only because of the osmotic effect.

Therefore, a composition (table 5) was prepared without adipic acid and ascorbic acid and with an amount of bicarbonate anion (e.g. sodium bicarbonate) less than 15% by weight, relative to the total weight of the composition.

For example, 84 mg of sodium bicarbonate constitutes 1 millimole and the $CO_2$ that is released occupies a total volume of 25.4 ml at 37° C. and under atmospheric pressure. The quantity of citric acid was chosen in such a manner as to ensure complete release of the $CO_2$ from the sodium bicarbonate at the pH values observed after the tablet's dissolution.

The composition of table 5 showed problems when subjected to a compression step in order to prepare the tablets.

The powder (table 5) showed poor cohesive properties due to the use of corn starch in a formulation with a low moisture content. All of the tablets output by the compression machine were capped even before being passed through the deduster.

Following this compression test the Applicant proceeded to replace corn starch with a mixture containing [microcrystalline cellulose:arabinogalactan] in a ratio by weight preferably comprised from 1:1 to 3:1.

TABLE 1

| Selected strain | Deposit number | Deposit date | Depositor |
|---|---|---|---|
| *Lactobacillus salivarius* CRL 1328 | DSM 24441 | 4 Jan. 2011 | Probiotical SpA (under license from Cerela) |
| *Lactobacillus paracasei* CRL 1289 | DSM 24440 | 4 Jan. 2011 | Probiotical SpA (under license from Cerela) |

TABLE 1-continued

| Selected strain | Deposit number | Deposit date | Depositor |
|---|---|---|---|
| *Lactobacillus gasseri* CRL 1259 | DSM 24512 | 25 Jan. 2011 | Probiotical SpA (under license from Cerela) |
| *Lactobacillus crispatus* CRL 1251 | DSM 24438 | 4 Jan. 2011 | Probiotical SpA (under license from Cerela) |
| *Lactobacillus crispatus* CRL 1266 | DSM 24439 | 4 Jan. 2011 | Probiotical SpA (under license from Cerela) |
| *Lactobacillus acidophilus* CRL 1294 | DSM 24513 | 25 Jan. 2011 | Probiotical SpA (under license from Cerela) |
| *Lactobacillus fermentum* LF 5 | CNCM I-789 | 21 Jul. 1988 | Probiotical SpA |
| *Lactobacillus fermentum* LF 10 | DSM 19187 | 20 Mar. 2007 | Probiotical SpA |
| *Lactobacillus fermentum* LF 09 | DSM 18298 | 24 May 2006 | Probiotical SpA |
| *Lactobacillus fermentum* LF 11 | DSM 19188 | 20 Mar. 2007 | Probiotical SpA |
| *Lactobacillus paracasei* LPC 00 | LMG P-21380 | 31 Jan. 2002 | Probiotical SpA |
| *Lactobacillus plantarum* LP 01 | LMG P-21021 | 16 Oct. 2001 | Laboratorio Microbiologico Grana Provolone SRL |
| *Lactobacillus plantarum* LP 02 | LMG P-21020 | 16 Oct. 2001 | Laboratorio Microbiologico Grana Provolone SRL |
| *Lactobacillus pentosus* LPS 01 | DSM 21980 | 14 Nov. 2008 | Probiotical SpA |
| *Lactobacillus acidophilus* LA 02 | DSM 21717 | 6 Aug. 2008 | Probiotical SpA |
| *Lactobacillus rhamnosus* LR 04 | DSM 16605 | 20 Jul. 2004 | Probiotical SpA |
| *Lactobacillus rhamnosus* LR 05 | DSM 19739 | 27 Sep. 2007 | Probiotical SpA |
| *Lactobacillus rhamnosus* LR 06 | DSM 21981 | 14 Nov. 2008 | Probiotical SpA |
| *Lactobacillus paracasei* LPC 08 | DSM 21718 | 6 Aug. 2008 | Probiotical SpA |
| *Lactobacillus delbrueckii* LDD 01 (MB 386) | DSM 22106 | 10 Dec. 2008 | Probiotical SpA (Steve Jones srl) |
| *Lactobacillus reuteri* | DSM 17938 | | BioGaia |
| *Lactobacillus reuteri* LRE 01 | DSM 23877 | 5 Aug. 2010 | Probiotical SpA |
| *Lactobacillus reuteri* LRE 02 | DSM 23878 | 5 Aug. 2010 | Probiotical SpA |
| *Lactobacillus reuteri* LRE 03 | DSM 23879 | 5 Aug. 2010 | Probiotical SpA |
| *Lactobacillus reuteri* LRE 04 | DSM 23880 | 5 Aug. 2010 | Probiotical SpA |
| *Lactobacillus salivarius* LS03 | DSM 22776 | 23 Jul. 2009 | Probiotical SpA |
| *Lactobacillus plantarum* PR ci | LMG P-21022 | 16 Oct. 2001 | Laboratorio Microbiologico Grana Provolone SRL |
| *Lactobacillus plantarum* 776/2 hi | LMG P-21023 | 16 Oct. 2001 | Laboratorio Microbiologico Grana Provolone SRL |
| *Lactobacillus pentosus* 9/1 ei | LMG P-21019 | 16 Oct. 2001 | Laboratorio Microbiologico Grana Provolone SRL |

TABLE 2

| Composition | mg/tablet |
| --- | --- |
| Bacterial strains: *L. paracasei* LPC 00, *L. acidphilus* LA 02 and *L. salivarius* CRL 1328 with a concentration comprised from 20 to 100 × $10^9$ CFU/g | 58 |
| Fructo-oligosaccharides (FOS) | 327 |
| Arabinogalactan | 250 |
| Microcrystalline cellulose | 270 |
| Anhydrous calcium hydrogen phosphate | 95 |
| Mixture of glycerides | 65 |
| Citric acid | 64 |
| Sodium bicarbonate | 56 |
| Insoluble dietary fibre | 43 |
| Sucrose palmitate | 26 |
| Silicon dioxide | 26 |
| Magnesium stearate | 20 |
| TOTAL (1 tablet) | 1,300 |

TABLE 3

| Formulation | | (1) | (2) | (3) | (4) | (5) |
| --- | --- | --- | --- | --- | --- | --- |
| Table 2 | powder | 5.9 | 6.1 | / | 1.3 | 327 |
| | tablets w/ low degree of hardness (5-6 kp) | / | 5.6 | 8.2 | 1.2 | 328 |
| | tablets w/ high degree of hardness (10-12 kp) | / | 5.1 | 16.4 | 1 | 292 |

TABLE 4 inadequate composition

| Composition | mg/tablet |
| --- | --- |
| Bacterial strains: (*L. paracasei* LPC 00, *L. acidophilus* LA 02, *L. paracasei* CRL 1289 with a concentration comprised from 20 to 100 × $10^9$/gram) | 291 |
| Corn starch | 335 |
| Adipic acid | 268 |
| Sodium bicarbonate | 210 |
| Ascorbic acid | 100 |
| Magnesium stearate | 42 |
| Anhydrous lactose | 34 |
| Stearic acid | 12 |
| Silicon dioxide | 8 |
| TOTAL (1 tablet) | 1,300 |

TABLE 5

1,300 mg composition

| Components | mg/tablet |
| --- | --- |
| Bacterial strains: (*L. paracasei* LPC 00, *L. acidophilus* LA 02, *L. paracasei* CRL 1328 with a concentration comprised from 20 to $10^9$/gram) | 199 |
| Arabinogalactin | 300 |
| Galacto-oligosaccharides (GOS) | 315 |
| Corn starch | 315 |
| Insoluble dietary fibre | 43 |
| Citric acid | 38 |

TABLE 5-continued 1,300 mg composition

| Components | mg/tablet |
| --- | --- |
| Magnesium stearate | 34 |
| Sodium bicarbonate | 28 |
| Silicon dioxide | 18 |
| Stearic acid | 10 |
| TOTAL (1 tablet) | 1,300 |

The invention claimed is:

1. A method for treatment of a vaginal infection in a subject, the method comprising
administering to the subject an effective amount of an effervescent composition in solid form comprising:
an acid-base system comprising an organic acid and a salt of carbonate and/or bicarbonate anion; said salt being present in an amount comprised from 1 to 15% by weight, relative to the total weight of the composition,
a mixture comprising microcrystalline cellulose and arabinogalactan in a ratio by weight from 1:1 to 3:1,
at least one probiotic bacterial strain having the ability to reduce and/or eliminate the presence of pathogenic agents selected from the group comprising: *Candida albicans, Candida glabrata, Candida parapsilosis, Candida krusei, Candida tropicalis, Gardnerella vaginalis, Trichomonas vaginalis, Neisseria gonorrhoeae, Escherichia coli, Herpes simplex* and *Haemophilus ducreyi*
the administering performed to treat the vaginal infection.

2. The method in accordance with claim 1, wherein said composition is in the form of a tablet, ovule, lozenge or granules.

3. The method according to claim 1 wherein the organic acid is selected from the group consisting of citric acid, malic acid, tartaric acid, fumaric acid, lactic acid and mixtures thereof.

4. The method according to claim 1 wherein the salt of the carbonate and/or bicarbonate anion is selected from the group consisting of: sodium carbonate, potassium carbonate, calcium carbonate, magnesium carbonate, sodium glycine carbonate, sodium bicarbonate, potassium bicarbonate, calcium bicarbonate, magnesium bicarbonate, sodium lactate, potassium lactate, carbonate lactate and mixtures thereof.

5. The method according to claim 1, wherein the salt of carbonate and/or bicarbonate anion is present in an amount comprised from 3 to 13% by weight, relative to the total weight of the composition.

6. The method according to claim 1, wherein the acid-base system consists of sodium bicarbonate and citric acid, and wherein the sodium bicarbonate is present in an amount comprised from 3 to 13% by weight, relative to the total weight of the composition.

7. The method according to claim 1, wherein said at least one probiotic bacterial strain belongs to at least one species selected from the group consisting of: *Lactobacillus plantarum, Lactobacillus pentosus, Lactobacillus casei, Lactobacillus casei* ssp. *paracasei, Lactobacillus rhamnosus, Lactobacillus acidophilus, Lactobacillus delbrueckii, Lactobacillus delbrueckii* ssp. *bulgaricus, Lactobacillus delbrueckii* ssp. *delbrueckii, Lactobacillus fermentum, Lactobacillus gasseri, Lactobacillus reuteri, Bifidobacterium longum, Bifidobacterium bifidum, Bifidobacterium breve, Bifidobacterium animalis* ssp. *lactis, Bifidobacterium ado-* lescentis, *Bifidobacterium pseudocatenulatum, Bifidobacterium catenulatum* or *Bifidobacterium infantis*; said at least one bacterial strain is preferably selected from among: *Lactobacillus salivarius* CRL 1328, *Lactobacillus paracasei* CRL 1289, *Lactobacillus* gasseri CRL 1259, *Lactobacillus* crispatus CRL 1251, *Lactobacillus* crispatus CRL 1266, *Lactobacillus acidophilus* CRL 1294, *Lactobacillus paracasei* LPC 00, *Lactobacillus plantarum* LP 02 and *Lactobacillus fermentum* LF 10.

8. The method according to claim 1, wherein the vaginal infection is vaginitis, vaginosis, candidiasis, gonorrhoea, herpes and venereal ulcer.

9. A method to treat a vaginal infection in a subject, the method comprising
administering to the subject an effective amount of an effervescent tablet in solid form comprising:
an acid-base system comprising sodium bicarbonate and citric acid; said bicarbonate being present in an amount comprised from 1 to 15% by weight, relative to the total weight of the composition,
a mixture comprising microcrystalline cellulose and arabinogalactan in a ratio by weight from 1:1 to 3:1,
at least one probiotic bacterial strain having the ability to reduce and/or eliminate the presence of pathogenic agents selected from the group comprising: *Candida albicans, Candida glabrata, Candida parapsilosis, Candida krusei, Candida tropicalis, Gardnerella vaginalis, Trichomonas vaginalis, Neisseria gonorrhoeae, Escherichia coli, Herpes simplex* and *Haemophilus ducreyi*,
the administering performed to treat the vaginal infection.

10. The method according to claim 1, wherein the salt of the carbonate and/or bicarbonate anion is present in an amount comprised from 4 to 12% by weight, relative to the total weight of the composition.

11. The method according to claim 1, wherein the salt of the carbonate and/or bicarbonate anion is present in an amount comprised from 5 to 10% by weight, relative to the total weight of the composition.

12. The method according to claim 1, wherein the acid-base system consists of sodium bicarbonate and citric acid.

13. The method according to claim 12, wherein the sodium bicarbonate is present in an amount from 5 to 10% by weight, relative to the total weight of the composition.

14. The method according to claim 3, wherein the organic acid is citric acid.

15. The method according to claim 4, wherein the salt of the carbonate and/or bicarbonate anion is a salt of the bicarbonate anion.

16. The method according to claim 12, wherein the sodium bicarbonate is present in an amount from 4 to 12% by weight, relative to the total weight of the composition.

* * * * *